United States Patent [19]

Oda

[11] Patent Number: 4,555,398

[45] Date of Patent: Nov. 26, 1985

[54] SUSTAINED-RELEASE VASODILATOR

[75] Inventor: Yoshifumi Oda, Kohchiken, Japan

[73] Assignee: Chisso Corporation, Osaka, Japan

[21] Appl. No.: 534,622

[22] Filed: Sep. 22, 1983

[30] Foreign Application Priority Data

Oct. 5, 1982 [JP] Japan ............................. 57-175144

[51] Int. Cl.⁴ ..................... A61L 15/03; A61F 13/00; A61K 9/70
[52] U.S. Cl. ........................................ 424/19; 424/22; 424/28; 424/78; 424/83
[58] Field of Search ................................. 424/19–22, 424/32, 33, 78–83

[56] References Cited

U.S. PATENT DOCUMENTS

| | | | |
|---|---|---|---|
| 3,096,248 | 7/1963 | Rudzki | 424/33 |
| 3,279,996 | 10/1966 | Long et al. | 424/33 |
| 3,317,394 | 5/1967 | Fryklof et al. | 424/32 |
| 3,390,050 | 6/1968 | Speiser | 424/78 |
| 3,453,360 | 7/1969 | Hill | 424/78 |
| 3,692,896 | 9/1972 | Tsumura et al. | 424/78 |
| 3,737,521 | 6/1973 | Born | 424/22 |

*Primary Examiner*—Shep K. Rose
*Attorney, Agent, or Firm*—Wenderoth, Lind & Ponack

[57] ABSTRACT

A vasodilator product having a sustained releasing function is produced by mixing and kneading an atoxic agent having vasodilating activity with a setting or thermoplastic resin and then molding them to form the molded product.

Further, the vasodilator can be molded integratedly together with a medical device to be implanted into a human body. These vasodilators can be used not only for an operation of cerebral aneurysm, but also for drainage and vasodilator after microvascular anastomosis and endarterectomy.

6 Claims, No Drawings

SUSTAINED-RELEASE VASODILATOR

BACKGROUND OF THE INVENTION

This invention relates to a sustained-release vasodilator. More particularly, this invention relates to the novel vasodilator which is made to be of the sustained-release type by mixing an atoxic agent having vasodilating activity with a setting or thermoplastic resin and molding them.

The number of deaths caused by cerebrovascular diseases ranks second amongst the causes of deaths, and reached about 160 thousand persons per year in 1981. Among them intracerebral hemorrhage forms about 20% thereof, and subarachnoid hemorrhage forms about 10%. Particularly, subarachnoid hemorrhage occurs frequently in men of ages of from the forties to fifties. 72 Percent of subarachnoid hemorrhage is caused by cerebral aneurysm, and curing of it is carried out by a surgical operation. The surgical operation is, however, accompanied with late cerebral vasospasm at the frequency of from 30 to 50%. Prognosis of the disease complicated with such the cerebral vasospasm is not satisfactorily, and about half of the patients may have some deficit. Further, there are many cases in which cerebral aneurysm is found out several days after paroxysm and in which the level of consciousness is not good so that the operation is delayed after a certain waiting period because of fear as to complication of cerebrovascular vasospasm due to the operation. In such cases, patients may die frequently by re-rupture during the waiting period.

Although the cause of the late cerebrovascular vasospasm accompanied with subarachnoid hemorrhage has been said to be induced by the decomposed substance of hematid, the precise mechanism subsequent the said decomposition of it has not been made clear sufficiently. As curing methods thereof, conservative treatments were tried such as those of removing coagulated clot of subarachnoid space till the opposite side, by using the large quantity of steroid, phenoxybenzamine, or by using intentional hypertension therapy by means of dopamine jointly. However, none of these has succeeded in attaining an effective result. On the other hand, papaverine hydrochloride is known to be a strong cerebrovascular vasodilator and to increase cerebrovascular bloodflow upon dosing. It has, however, the disadvantage that its half-life is short due to its easily-decomposing property in liver and that in the case of peroral administration the decomposition occurs particularly quickly. Intravenous injection is ineffective for improving cerebral bloodflow because of causing hypertension due to expansion of total peripheria vessel. Large quantity systemic administration has the danger of A-V block formation and fear of side-effects such as nausea, anoreria, constipation, vertigo, headache and perspiration, etc. As to administration by intra-arterial injection, there is a large danger of embolization. Under such conditions, curing of late cerebrovascular vasospasm by administration of papaverine hydrochloride has not been sufficiently effective. (On the other hand, transient but clear remission of vasospasm is noticed by applying papaverine hydrochloride to the exposed vessel during an operation.) No complete remedy which has sure curing effect, and long lasting period of its effectiveness has been known hitherto as to the curing of late cerebrovascular vasospasm accompanied with subarachnoid hemorrhage. The inventor has studied about the effective remedies for late cerebrovascular vasospasm variously to conclude that the long-lasting sustained release type of vasodilator is effective for solving the problem. That is, an agent which is made to be a sustained-release type by mixing an atoxic agent having vasodilating activity with a setting or thermoplastic resin and then set-molding or molding them is found to be effective as the vasodilator for the delayed cerebrovascular diseases.

In general, methods for making agents to be the sustained-release types are divided roughly into two groups, i.e. physically gradual release and chemically gradual release methods. The latter has, however, troublesome problems in aspects relating to elucidation of its mechanism or confirmation of safety. On the contrary, the former, i.e. the gradually releasing method by physical method, is considered to be the more desirable one for this invention because of less problems. As such physical methods, there are mentioned the following two processes: (a) the process to capsulate the agent by covering it with a film-type covering material, and (b) the process to mix the agent into a high polymer material to disperse and then mold them to pellets. Pelleting is decided to be the desirable method for the remedy of late cerebrovascular vasospasm, etc. according to the invention, since the necessary period to release the agent gradually is about from 2 to 4 weeks.

As seen clear from the above-mentioned description, an object of the invention is to provide a sustained-release vasodilator, particularly the said vasodilator as a remedy for late cerebral vasospasm. Other objects will be become clear from the following description.

SUMMARY OF THE INVENTION

The invention (composed of two aspects) has the following (1) and (2) main constituents.
(1) The sustained release vasodilator which is made by mixing an atoxic agent having vasodilating activity with a setting or thermoplastic resin and molding.
(2) The sustained-release vasodilator which is made by mixing an atoxic agent having vasodilating activity with a setting or thermoplastic resin and molding the mixture integratedly together with a medical device to be implanted into body.

DETAILED DESCRIPTION OF THE INVENTION

As the atoxic agent having vasodilating activity (hereinafter also referred as the vasodilator), any agent which is confirmed to be atoxic, that is, which has safety for higher animals such as human body basically may be used. Concretely, there are mentioned papaverine hydrochloride, nicardipine hydrochloride, diltiazem, cinnarizine, cyclandelate, bencyclane fumarate, peutoxifylline, hidergine, meclofenoxate hydrochloride and pyrithioxine hydrochloride, etc. which are used conventionally. The mixing ratio of the agent in the sustained-release vasodilator according to the invention will differ owing to the specific use, that is the necessary effective amount of the agent at the diseased part. Also it is necessary to maintain the below mentioned tensile strength desired for the sustained-release vasodilator according to the invention. The agent may be used generally within the range of from 1 to 60 weight %, preferably from 2 to 50 weight %. Speaking about the above-mentioned effective amount at the diseased part, the stronger the activity of the vasodilator is, the lower the mixing ratio may be.

The setting or thermoplastic resin used according to the invention is necessary to be atoxic medically and stable when embedded into body, and have sufficient mechanical strength so as not to be broken while it remains in body and when removed from the body. Furthermore, the vasodilator according to the invention is necessary to have sufficient flexibility not to cause any useless mechanical stimulus to body, since as used it remains in the body. Any resin which satisfies the above-mentioned conditions may be used. As the setting resins, there are mentioned, for example, silicone resin, cyanoacrylate resin, epoxy resin, and polyimide resin, etc. As the thermoplastic resins, there are mentioned, for example, polystyrene resin, polyolefin resin, polyvinyl chloride resin, cellulose acetate resin, polyamide resin, polyurethane resin and acrylic resin. These resins should maintain sufficient strength for use by remaining in the body, i.e. about from 10 to 15 Kg/cm$^3$, when mixed with the vasodilator at the specified ratio and molded.

The above-mentioned vasodilator and setting or thermoplastic resin are mixed and molded. That is, the said molding method is to mix the monomer (note; prepolymer) with the vasodilator at the specified ratio, then mold and set them by mixing with the setting agent in the case of using the setting resin. In the case of using a resin having a long setting period, the above-mentioned monomer, the vasodilator and the setting agent may be mixed at the same time.

In a case of using the thermoplastic resin in the said molding procedure, a resin which has been plasticized or dissolved beforehand by mixing with the necessary plasticizer or solvent is mixed with the vasodilator, kneaded and molded. As the said necessary plasticizer or solvent, those known in the art may be used in the known manner. The mixing ratio of the afore-mentioned thermoplastic resin plasticized or dissolved and the vasodilator is as described above, and conditions of mixing and kneading are, for example, such that they are mixed and kneaded at from 0° to 100° C., preferably from 20° to 70° C., for from 10 minutes to 10 hours, preferably from 30 minutes to 5 hours, using a compounding device such as kneader or ribbon blender. The conditions of mixing and kneading are almost the same in the above-mentioned case of the setting agent and the vasodilator, except that the mixing and kneading periods are shorter, preferably from 20 minutes to 2 hours.

As described above, the mixture of the resin and the vasodilator which has been mixed and kneaded according to the invention is then poured or pressed into a specified mold to set under the specified conditions (in the case of the setting resin), or to mold by the known process such as extruded molding or injection molding, etc. (in the case of the thermoplastic resin). The solvent used in the latter case separates upon heating under reduced pressure, etc. and is recovered. The treating temperature and atmosphere during the said mixing and kneading as well as those under the subsequent molding conditions should be selected such that the mixed vasodilator cannot be oxidized or decomposed. Therefore, in the case of normal temperature, setting atmosphere of air may be used, but mixing and kneading or setting at the temperature above 50° C. may be carried out preferably under an inert gas atmosphere such as nitrogen gas, argon or carbon dioxide. For similar reasons, the upper limit of the temperature during mixing and kneading, molding or setting should not exceed the temperature at which thermal decomposition of the individual vasodilator takes place markedly. Molded products thus obtained are pellets having various forms such as column, disc, square pillar, square plate, cone, pyramid, circle, cylinder, drum and oval forms. Size or volume thereof is, for example, about from 1 to 5 mm$\phi$, from 2 to 40 mmL and from 20 to 800 mm$^2$ in the case of column form for its usage objects.

By using the pellets according to the invention (the first aspect) thus obtained by embedding in the diseased part directly, the vasodilator in the pellets may be released gradually to display the objective effect of the medicine.

On the other hand, according to the second aspect of this invention, the usage and the effect of the first aspect may be specialized and improved by molding integratedly a medical device and embedding together with the above-mentioned pellets. As the medical device, there is mentioned, for example, a drainage-tube molded from the thermoplastic resin. In such the device, the drainage-tube is used for draining blood or spinal fluid trapped in the epidural space after bleeding owing to cerebral aneurysm, intraventricular hemorrhage, subarachnoid hemorrhage, etc. The sustained-release vasodilator according to the second aspect may be obtained by molding integratedly the pellet according to the first aspect of this invention at the top of the drainage-tube to bind them together. As will become clear from the illustration described above, when it is applied to human body, not only two objects, that is, draining of blood after operation and prevention of the late cerebrovascular vasospasm, are attained simultaneously, but also a more superior result is obtained synergetically than in the case where these components or agents are applied individually at same diseased part. Such the integrated moldings, that is the products of this invention (the products of the second aspect) may be used not only for the said operation of cerebral aneurysm, but also for drainage and vasodilator after microvascular anastomosis and endarterectomy. Practical value of the moldings is, therefore, important.

This invention is illustrated by the following examples, but those are not intended to limit this invention.

Example 1

| | |
|---|---|
| Silastic elastomer MDX-4-4210 (product of Dow Corning Co.) | 5.4 g |
| Setting agent for the elastomer | 0.6 g |
| papaverine hydrochloride | 4.0 g |

The above-mentioned components are mixed and kneaded at room temperature, and then poured into a mold to set and form columns having a diameter of 3 mm and a length of 20 mm. (setting condition; 40° C. for 5 hours, specific gravity ≈ 1.12) The column-form pellets are introduced into a test tube and a dissolution test of papaverine hydrochloride at 37° C. is carried out by adding 10 ml of physiological saline. The 10 ml of physiological saline is changed every day. Dissolved amounts per day are shown in the Table.

| lapsed days | 1 | 2 | 3 | 4 | 5 | 6 | 8 | 15 |
|---|---|---|---|---|---|---|---|---|
| dissolved | 4.9 | 3.8 | 2.7 | 2.5 | 2.2 | 2.1 | 2.0 | 1.9 |

-continued

| lapsed days | 1 | 2 | 3 | 4 | 5 | 6 | 8 | 15 |
|---|---|---|---|---|---|---|---|---|
| amount, mg | | | | | | | | |

Zoological tests are carried out using two monkeys (males with weights of 7.1 Kg and 8.0 Kg).

First, the monkey with a weight of 7.1 Kg is subjected to a craniotomy under narcosis, a pellet containing papaverine hydrochloride is introduced in the subarachnoid cavity and at the same time a silicone tube is arranged to enable the pouring of blood into the subarachnoid cavity. The monkey with a weight of 8.0 Kg is subjected to craniotomy under narcosis and only a silicone tube is arranged to enable pouring of blood into the subarachnoid cavity. For two monkeys, after collecting fresh blood from the arteries of each monkey, 9 ml of their own blood is poured via the silicone tubes arranged beforehand into the subarachnoid cavities gradually for 10 minutes to form cerebrovascular vasospasm caused by subarachnoid hemorrhage. Speaking about general symptoms of the monkey without arrangement of pellet, this monkey is unable to stand and crouches. It has a poor appetite and shows occasionally a tremor. About 30% dilation of the basilar artery is confirmed by retrograde brachial angiography under general anesthesia. On the contrary, for the monkey to which the pellet containing paraverine hydrochloride has been administrated beforehand, vasospasm of cerebrovascule cannot be found and it tends to be rather expansively, so that nervous symptoms are lighter.

Example 2

| Silastic elastomer MDX-4-4210 | 8.7 g |
|---|---|
| setting agent for the elastomer | 0.8 g |
| nicardipine hydrochloride | 0.5 g |

The above-mentioned components are kneaded sufficiently and then molded into column-form pellets having a diameter of 3 mm and a length of 20 mm.

Two narcotized dogs (adult mongrel dogs with weights of 8.5 Kg and 11.0 Kg) are subjected to cisternal puncture using injection needles to collect 5 ml of cerebrospinal liquid and thereafter 5 ml of their own fresh blood collected from femoral arteries are poured into cisterna magmas over about 10 minutes.

Vasospasm of basilar arteries are found to occur after 1 day by means of X-ray photography, and the diameters of the basilar arteries are shrunk by about 28%. As to the general symptoms at that time, they can stand up but they display paretic gait and ataxic gait. One dog (the dog with a weight of 8.5 Kg) is subjected to craniotomy under narcosis, and the said pellet is introduced into the part in which is found the occurrence of vasospasm. The diameter of spastic vascule recovers approximately to the normal vascular diameter before vasospasm by vascular photography by the next day.

On the contrary, it takes about 6 days for recovery of the vasospasm of vascule approximately to the normal vascular diameter for the dog to which the sustained-release type pellet containing nicardipine has not been administered.

Example 3

A female patient (49 years old) who has been hospitalized suffering from Ruptured IC-PC (internal carotid-posterior communicating artery) aneurysm is subjected to craniotomy on the first day, and neck clipping of the ruptured vessel is carried out. Furthermore the large amount of blood mass trapped in basilar cistern is removed, and after washing a drainage-tube equipped with a pellet (30 mm×3 mmφ) containing 40% of papaverine hydrochloride is inserted.

Although her consciousness before the operation was such that she could only open her eyes when her name was called her consciousness becomes clear after the operation. The drainage-tube is removed on the tenth day, and the patient leaves hospital after two weeks. Concentrations of papaverine hydrochloride in pulpa liquor obtained from the drainage are shown as follows:

| after 15 hours | (drainage open) | 190 μg/ml |
|---|---|---|
| on second day | (drainage closed) | 90 μg/ml |
| on third day | (drainage open) | 20 μg/ml. |

I claim:

1. A sustained release vasodilator product in molded form which comprises (1) a vasodilating effective amount of an atoxic agent having vasodilating activity selected from at least one member of the group consisting of papaverine hydrochloride, nicardipine hydrochloride, diltiazem, cinnarizine, cyclandelate and bencyclane fumarate and (2) a member selected from the group consisting of
   (a) at least one setting resin selected from the group of silicone resin, cyano-acrylate resin, epoxy resin and polyimide resin, and
   (b) at least one thermoplastic resin selected from the group of polystyrene resin, polyolefin resin, polyvinyl chloride resin, cellulose acetate resin, polyamide resin, polyurethane resin and acrylic resin, said molded product being prepared by mixing and kneading the said atoxic agent with the setting or thermoplastic resin and subsequently molding the resultant mixture.

2. A sustained release vasodilator product which comprises a molded product according to claim 1 which is further integratedly molded with a medical device which is to be implanted into a human body.

3. A product according to claim 1 wherein from 1 to 60% by weight of the said atoxic agent and a monomer of the said setting resin are mixed and kneaded for 20 minutes to 2 hours at 0° to 100° C.

4. A product according to claim 1 wherein from 1 to 60% by weight of the said atoxic agent and the thermoplastic in plasticized form are mixed and kneaded for a period of 10 minutes to 10 hours at 0° to 100° C.

5. A product according to claim 1 wherein the atoxic agent is papaverine hydrochloride and the resin is silicone resin.

6. A product according to claim 2 wherein the atoxic agent is papaverine hydrochloride and the resin is silicone resin.

* * * * *